US009185857B2

(12) United States Patent
Willits et al.

(10) Patent No.: US 9,185,857 B2
(45) Date of Patent: *Nov. 17, 2015

(54) FLAVONOL EXPRESSING DOMESTICATED TOMATO AND METHOD OF PRODUCTION

(75) Inventors: Michael G. Willits, Apex, NC (US); Vincenzo Deluca, Fonthill (CA); Gerson Graser, Cary, NC (US); Catherine M. Kramer, Hillsborough, NC (US); Rogerio T. N. Prata, Chapel Hill, NC (US)

(73) Assignee: Syngenta Participations AG, Basel (CH)

( * ) Notice: Subject to any disclaimer, the term of this patent is extended or adjusted under 35 U.S.C. 154(b) by 483 days.

This patent is subject to a terminal disclaimer.

(21) Appl. No.: 12/938,849

(22) Filed: Nov. 3, 2010

(65) Prior Publication Data

US 2011/0113500 A1    May 12, 2011

Related U.S. Application Data

(63) Continuation of application No. 10/517,903, filed as application No. PCT/US03/18122 on Jun. 6, 2003, now Pat. No. 7,851,680.

(60) Provisional application No. 60/389,061, filed on Jun. 14, 2002.

(51) Int. Cl.
*A01H 5/08* (2006.01)
*A01H 1/00* (2006.01)
*C12N 15/52* (2006.01)

(52) U.S. Cl.
CPC ........................................ *A01H 5/08* (2013.01)

(58) Field of Classification Search
None
See application file for complete search history.

(56) References Cited

U.S. PATENT DOCUMENTS 7,851,680 B2 * 12/2010 Willits et al. .............. 800/317.4

FOREIGN PATENT DOCUMENTS

| WO | WO 99/14351 | 3/1999 |
| WO | WO 99/37794 | 7/1999 |
| WO | WO 00/04175 | 1/2000 |
| WO | WO 00/37652 | 6/2000 |
| WO | WO 00/53771 | 9/2000 |

OTHER PUBLICATIONS

Stewart et al (J Agric Food Chem 48: 2663-2669, 2000).*
Goffreda et al (Theor Appl Genet 78: 210-216, 1989).*
Muir et al (Nature Biotechnology 19: 470-474, 2001).*
Allard (Interspecific hybridization in plant breeding. In Principles of plant breeding, Chapter 34, pp. 434-443, 1960).*
Bino et al., New Phytologist, May 2005, 166, 2, 427-438.
Bovy et al., The Plant Cell, 2002, 14, 2509-2526.
Cook et al., Nutritional Biochemistry, 1996, 7, 66-76.
Crozier et al., Journal of Agricultural and Food Chemistry, 1997, 45, 3, 590-595.
Eshed et al., Theoretical and Applied Genetics, 1996, 93, 5/6, 877-886.
Eshed et al., Genetics, Aug. 1996, 143, 1807-1817.
Muir et al., Nature Biotechnology, 2001, 19, 470-474.
Rice-Evans et al., Free Radical Research, 1995, 22, 375-383.
Rice-Evans et al., Trends in Plant Science, 1997, 2, 152-159.
Stewart et al., Journal of Agricultural and Food Chemistry, 2000, 48, 2663-2669.
Verhoeyen et al., Journal of Experimental Biology, 2002, 53, 377, 2099-2106.
Willits et al., Journal of Agricultural and Food Chemistry, Feb. 23, 2005, 53, 4, 1231-1236.
Yen et al., Theoretical and Applied Genetics, Nov. 1997, 95, 7, 1069-1079.
Goffreda et al., Theor Appl Genet, 1989, 78, 210-216.
Peralta et al., American J Botany, 2001, 88, 10, 1888-1902.
Allard, Interspecific hybridization in plant breeding. In Principles of Plant Breeding, 1960, Chapter 34, 434-443.
Mills et al., Plant Cell Reports, 1996, 15, 634-636.
Wikipedia. http://en.wikipedia.org/wiki/Quercetin. printed Jan. 6, 2008.
File History for U.S. Appl. No. 10/517,903.

* cited by examiner

*Primary Examiner* — Phuong Bui
(74) *Attorney, Agent, or Firm* — Karen A. Magri (57) ABSTRACT

The present invention includes non-transgenic domesticated tomato plants that express flavonols in the flesh and peel of the tomato fruit, and includes the seeds and fruits of such plants. The method of the invention includes assaying tomato plants for expression of one or more of the flavonol biosynthesis genes in the flesh and/or expression of CHI in the peel. The method of the invention includes selecting wild tomato species that express CHI in the fruit peel, and/or one or more genes of the flavonol biosynthesis pathway in the flesh, and introgressing the genetic factors responsible for this expression from the wild tomato species into a domesticated tomato plant using traditional breeding techniques.

8 Claims, 5 Drawing Sheets

FLAVONOL EXPRESSING DOMESTICATED TOMATO AND METHOD OF PRODUCTION

CROSS REFERENCE TO RELATED APPLICATIONS

This application is a continuation of U.S. patent application Ser. No. 10/517,903, filed Dec. 20, 2004, now U.S. Pat. No. 7,851,680 B2, which is a U.S. national phase application of International Application No. PCT/US03/18122, filed Jun. 6, 2003, which claims priority to U.S. Application No. 60/389,061, filed Jun. 14, 2002.

FIELD OF THE INVENTION

This invention is in the field of tomato breeding, specifically relating to the production of domesticated tomato plants that accumulate flavonols in the fruit peel and flesh, thereby significantly increasing the total content of health beneficial flavonols in the tomato fruit.

BACKGROUND OF THE INVENTION

Tomato (*Lycopersicon esculentum*) is one of the major vegetables in human diets. Use of traditional breeding techniques has incorporated numerous beneficial traits into the tomato, including such traits as extended shelf-life, disease resistance, and sugar content. There is also a significant interest in the industry to develop tomatoes that express compounds that can impart health benefits to humans. These health benefits can be delivered by development of dietary supplements containing the extracted components and by production of these components directly in a food source for human consumption.

Flavonoids, especially flavonols such as quercetin and kaempferol, are believed to impart a number of health benefits if ingested in sufficient quantities. Studies have shown that flavonoids possess antioxidant and anticancer activities (Rice-Evans et al., Free Radical Research, 22:375-383, 1995). Additional health benefits include anti-platelet aggregation (Rice-Evans et al., Trends in Plant Science, 2:152-159, 1997), decreased blood viscosity, reduction in the severity of inflammation and allergies (Cook et al., Nutritional Biochemistry 7:66-76, 1996), as well as other health beneficial effects (e.g. antiviral activity, anti-tuberculosis activity). Therefore, there is significant interest in developing plants accumulating high levels of flavonoids, especially flavonols.

The flavonol, quercetin, is biosynthesized from p-coumaryl-CoA ($C_6C_3$) and malonyl-CoA ($C_3$). In a polyketide synthesis reaction (catalyzed by chalcone synthase) the phenylpropane unit acts as a starting compound for the successive addition of three acetate units ($C_2$—from malonyl-CoA) to form, after cyclization, naringenin chalcone ($C_6C_3C_6$). The flavone naringenin is generated by formation of the heterocycle C-ring, a reaction that is catalyzed by chalcone isomerase. Quercetin is then synthesized by successive oxidization reactions of naringenin that yield a double bond between C-2 and C-3 and hydroxylation of C-3 and C-3'. These oxidation reactions are carried out by flavanone-3-hydroxylase, flavonol synthase and flavonol-3',5'-hydroxylase. The final products of the pathway, quercetin mono- and di-glycosides (isoquercitrin and rutin, respectively), are formed through the action of O-glycosyltransferases. The mono-glucoside of the flavonol kaempferol, which is found only in trace amounts in tomato, is synthesized in the same way but with the omission of the hydroxylation in the C-3' position.

Studies have shown, and we have confirmed, that in domesticated tomato varieties the chalcone isomerase (CHI) gene is present but not expressed in the fruit peel. Additionally, none of the flavonol biosynthesis genes are expressed in the flesh of the tomato fruit. Both results clearly explain the observed lack of flavonol accumulation in domesticated tomato fruits. Thus, it has been assumed in the art that obtaining high flavonol tomatoes cannot be accomplished by using traditional breeding techniques, as CHI expression would remain blocked and the fruit flesh would continue to accumulate insignificant levels of flavonols. Modern recombination technology, or genetic modification, is now being used to selectively modify the flavonoid pathway to produce plants with elevated levels of flavonols. However, to date, enhanced expression of flavonols is substantially limited to the tomato peel. See, for example, Muir, S. R. et al. *Overexpression of petunia chalcone isomerase in tomato results in fruit containing levels of flavonols* Nature Biotechnology, 19:470-474 (2001) (Muir et al. detected approximately 0.5 mg/kg fresh weight [0.0045 μg/mgdwt] of rutin in tomato flesh, which was at the limit of detection); WO 00/37652, Flavonoid Biosynthetic Enzyme; WO 99/37794, Methods and Composition for Modulating Flavonoid Content; WO 99/14351, Isoflavone Biosynthetic Enzymes; WO 00/53771, Genetic Manipulation of Isoflavonoids; and WO 00/04175 Methods and Composition for Modulating Flavonoid Content. Table 1 shows the flavonol accumulation in the fruit of transgenic and non-transgenic tomato plants as revealed by various research groups. The high levels of flavonol accumulation of the cherry tomato is due to the high proportion of peel to flesh in cherry tomatoes compared to standard sized tomatoes.

TABLE 1

| Source | Tomato Variety | μg/mg dry weight (total fruit) | μg/mg dry weight (flesh) | μg/mg dry weight (peel) | mg flavonols per 57 g tomato (estimate) |
|---|---|---|---|---|---|
| SYNGENTA Domesticated | ZTV 840 | 189 | 0.1 | 3.0 | 1.2 |
| UNILEVER (CHI/ Petunia) Muir, S., Collins, G., Robinson, S., Hughes, S., Bovy, A., DeVos, R., van Tunen, A., Verhoeyen, M. (2001) Nature Biotechnology, 19: 470-474 | Transgenic  Nontransgenic | 4,000 | | 17 (used 2 mm thick peel) 0.05 used 2 mm thick peel) | 25 |
| Non-Transgenic - Crozier, A., Lean, M., McDonald, Black, C. (1997) J. Agric. Food Chem, 45: 590-595 | Different varieties | | | | 6 |

TABLE 1-continued

| Source | Tomato Variety | μg/mg dry weight (total fruit) | μg/mg dry weight (flesh) | μg/mg dry weight (peel) | mg flavonols per 57 g tomato (estimate) |
|---|---|---|---|---|---|
| Non-Transgenic - Crozier, A., Lean, M., McDonald, Black, C. (1997) J. Agric. Food Chem, 45: 590-595 | Cherry tomatoes | | | | 2.3 |
| Non-Transgenic - Stewart, A., Bozonnet, S. Mullen, W., Jenkins, G., Lean, M., Crozier, A. (2000) J. Agric. Food Chem., 49: 2663-2669 | Different varieties | | 0.01 | 0.72 | 1.2 |

The present invention recognizes that there is a significant need to produce domesticated tomato plants, using traditional breeding techniques, that accumulate significant amounts of flavonols in the peel, as well as in the flesh, of the tomato fruit.

There is also a need for a method to identify tomato germplasm that expresses the CHI gene in the peel of the tomato fruit.

There is a further need to identify tomato germplasm that expresses the flavonol biosynthetic pathway in the flesh of the tomato fruit.

An additional need in the art is to identify tomato germplasm that expresses the CHI gene in the peel of the tomato fruit and the flavonol biosynthetic pathway in the flesh of the tomato fruit.

SUMMARY OF THE INVENTION

The present invention relates to tomato plants that accumulate high levels of flavonols in the fruit. In particular, the present invention provides tomato plants that accumulate flavonols in the peel of the tomato fruit. Preferably, the present invention provides tomato plants, generated using traditional breeding techniques, which accumulate flavonols in the flesh and peel of the tomato fruit. The present invention includes the seeds and fruit, and parts thereof, of such plants.

The method of the invention further includes a method for assaying wild tomato plants for expression of CHI in the fruit peel and/or of one or more of the genes of the flavonol biosynthesis pathway in the fruit flesh. The method of the invention further includes selecting those plants that express CHI in the fruit peel and/or the genes of the flavonol biosynthesis pathway in the flesh, and introgressing, using traditional breeding techniques, the genetic factors responsible for such expression from those plants into a domesticated tomato plant.

The invention further includes non-transgenic domesticated L. esculentum plants that accumulate flavonol in the fruit flesh of the plant at levels greater than 0.5 μg/mgdwt.

The invention further includes non-transgenic domesticated L. esculentum plants that accumulate flavonol in the fruit flesh of the plant at levels greater than 1.0 μg/mgdwt.

The invention further includes non-transgenic domesticated L. esculentum plants that accumulate flavonol in the fruit flesh of the plant at levels greater than 1.5 μg/mgdwt.

The invention further includes non-transgenic domesticated L. esculentum plants that accumulate flavonol in the fruit flesh of the plant at levels greater than 2.0 μg/mgdwt.

The invention further includes the L. esculentum plants wherein the flavonol content in the fruit peel is at least approximately 5 μg/mgdwt.

The invention includes the L. esculentum plants wherein the flavonol content in the fruit peel is at least approximately 10 μg./mgdwt.

The invention includes the L. esculentum plants wherein the flavonol content in the fruit peel is at least approximately 17 μg./mgdwt.

The invention includes the fruit of the L. esculentum plants that accumulate flavonol in the fruit flesh of the plant at levels greater than 0.5 μg/mgdwt.

The invention includes seed of the L. esculentum plants that accumulate flavonol in the fruit flesh of the plant at levels greater than 0.5 μg/mgdwt.

The invention includes fruit of the L. esculentum plants that accumulate flavonol in the fruit flesh of the plant at levels greater than 0.5 μg/mgdwt.

A L. esculentum plant, or parts thereof, produced by growing the seed of plants that accumulate flavonol in the fruit of the plant at levels greater than 0.5 μg/mgdwt.

The invention also includes a method of making a non-transgenic L. esculentum plant accumulating flavonols in the peel and flesh of the fruit of said plant comprising the steps of:
  a) crossing wild accessions of Lycopersicon that express CHI in the peel and that express the genes of the flavonol biosynthetic pathway in the flesh with a L. esculentum plant to produce a hybrid plant;
  b) harvesting fruit from the hybrid plant; and
  c) collecting seed from the fruit harvested in step b).

The invention includes a method of making a non-transgenic L. esculentum plant including the step of screening Lycopersicon accessions for expression of CHI in the peel or for expression of the genes of the flavonol biosynthetic pathway in the flesh.

Also included in the invention is a method of making a non-transgenic L. esculentum plant wherein the Lycopersicon species are selected for crossing with a L. esculentum plant are L. chilense or L. pennellii, or any other wild tomato species that express the genes of the flavonol biosynthetic pathway in the flesh and CHI in the peel of the fruit.

The invention includes a method of making a non-transgenic L. esculentum plant, wherein the accessions selected for crossing are LA1963, LA2884, and LA1926.

The invention further includes a non-transgenic domesticated L. esculentum plant comprising a genetic factor that up-regulates the flavonol biosynthesis pathway in the fruit flesh of the plant.

The invention further includes a non-transgenic domesticated L. esculentum plant comprising a genetic factor that restores CHI expression in the fruit peel of the plant.

The invention further includes inbred and hybrid L. esculentum plants developed using traditional breeding techniques comprising genetic factors that express the genes of the flavonol biosynthetic pathway in the flesh and CHI in the peel of the fruit, and further includes *L. esculentum* plants that are homozygous or heterozygous for these genetic factors.

Fruits containing the increased levels of flavonols of the present invention provide substantial health benefits, including the benefits of antioxidant activity, anticancer activities, anti-platelet aggregation, and decreased blood viscosity.

DETAILED DESCRIPTION OF THE INVENTION

"Domestication" or "domesticated" refers to a plant that has different genetic and structural characteristics from wild plants due to human selection.

"Wild" refers to a plant in or out of captivity that has not been subject to breeding to alter it from its native (wild) state.

"Accession" refers to a distinct, uniquely identified sample of seeds or plants that is maintained as part of a germplasm collection.

"Germplasm" refers to seeds, plants, or plant parts that are useful in crop breeding, research, or conservation.

"Variety" refers to a plant type within a species that is distinguishable by one or more characters. When reproduced from seeds or by asexual means (e.g. cuttings) its distinguishing characters are retained.

"Introgression" refers to the insertion of the genes of one plant into the gene pool of another. This can occur when two plants interbreed to produce fertile hybrids. These can then back-cross with individuals of one of the parent plants.

"Species" refers to a taxonomic subdivision; a group or populations of organisms that actually or potentially interbreed and are reproductively isolated from other such groups. A particular species can contain many different accessions.

This invention relates to tomato breeding, including the production of a domesticated tomato that accumulates flavonols in the peel and flesh of the tomato fruits. Because the tomato peel is such a small fraction of the entire tomato, extremely large quantities of peel-localized flavonol must be produced to get a significant dose in each tomato. With entire fruit production, flavonol levels are significantly increased according to the invention. The invention provides a unique method for enhancing accumulation of flavonol in tomato fruit that includes the step of identifying germplasm that expresses CHI in the fruit peel, and also includes identifying germplasm that expresses the genes of the flavonol biosynthetic pathway in the flesh. According to the method of the invention, a CHI gene that expresses chalcone isomerase in tomato fruit peels has been identified in some wild *Lycopersicon* species. Also according to the invention, wild *Lycopersicon* species are identified that express the genes of the flavonol biosynthetic pathway in the flesh, i.e., in these species the flavonol biosynthetic pathway is upregulated in the flesh of the tomato fruit. According to the invention, wild *Lycopersicon* species are identified that express the CHI gene in the tomato fruit peel and that also express the genes of the flavonol biosynthetic pathway in the fruit flesh.

The invention further includes using traditional breeding techniques to generate F1 hybrids by crossing the domesticated tomato *L. esculentum* with *L. pennellii*, wherein the resulting F1 hybrid plants produce fruit that for the first time accumulate high levels of flavonols in both the tomato fruit flesh and peel.

Example I

Plant Growth and Tissue Harvest

Plants were grown in a non-soil potting mix in a greenhouse at 78 to 82° F., with 75 to 90% relative humidity, and a 16-hour photoperiod. Members of accessions LA1963, LA2884, LA1926, LA111, LA1292, and LA 1330 are self-incompatible and were pollinated by sib crossing.

Leaf tissue from each plant was harvested and frozen in liquid nitrogen. Tomato fruits were harvested at various stages of ripening: green mature, breaker, and ripe for red maturing lines; unripe and ripe for green maturing lines. Large tomatoes (*L. esculentum* and *L. esculentum* v. *cerasiforme*) were peeled with a knife. The peel tissue was frozen in liquid nitrogen. The seeds and locular gel were removed from the remaining tissue, and the combined pericarp and placental tissue were designated as flesh tissue and also frozen in liquid nitrogen. The peel tissue was removed from the small wild tomatoes by squeezing the tomatoes between forefinger and thumb. The internal tissues (seeds, locular gel, pericarp, and placental tissue) were collected together, designated as flesh tissue, and frozen in liquid nitrogen. The peel tissue was frozen in liquid nitrogen as well. Frozen tissue was stored at −80° C.

Example II

Northern Blot Analysis

Expression levels of flavonol biosynthesis genes in *L. esculentum* were determined by Northern analysis. Leaf tissue was finely ground in a mortar and pestle under liquid nitrogen. Fruit tissue was finely ground in a coffee grinder under liquid nitrogen. Total RNA was isolated from ground tissue according to the protocol of Lagrimini et al. (1987). For Northern blot analysis, 10 µg of RNA was loaded onto formaldehyde agarose gels and electrophoresed at 240 volts for 45 minutes. RNA was then transferred onto Hybond-N+ nylon membranes (Amersham Pharmacia Biotech).

cDNA fragments for chalcone synthase-A (CHS-A), chalcone isomerase (CHI), flavanone 3-hydroxylase (F3H), and flavonol synthase (FLS) were isolated from *L. esculentum*, *L. pimpinellifolium* (LA1261), and *L. parviflorum* (LA1326). The fragments were obtained from leaf RNA by RT-PCR. All fragments were sequenced and compared across species. For each cDNA, the fragments were at least 98% identical across species. Therefore probes were prepared from cDNA fragments of *L. esculentum*.

Probes were labeled with $^{32}P$ and purified according to the instruction for the Rediprime II Random Prime Labeling System and ProbeQuant G50 Micro Columns (Amersham Pharmacia Biotech). Blots were hybridized overnight at 65° C. in 1% BSA, 0.5M sodium phosphate buffer, 7% SDS, 1 mM EDTA. Blots were washed 2 times at 65° C. in 0.5% BSA, 40 mM sodium phosphate buffer, 1% SDS, 1 mM EDTA, and 2 times in 40 mM sodium phosphate buffer, 1% SDS, 1 mM EDTA. Blots were then exposed to X-ray film overnight at −80° C.

Figure 1:
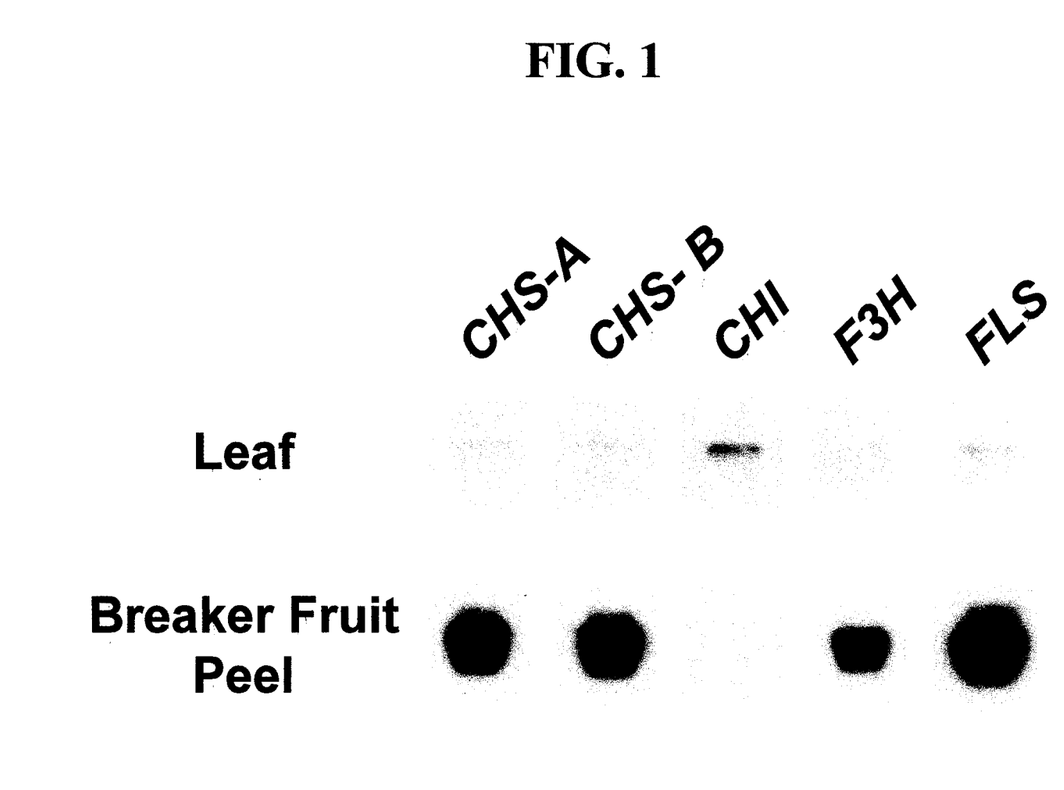
FIG. 1 shows flavonol biosynthetic gene expression in the leaf and breaker fruit peel of *L. esculentum* by Northern blot analysis.

Total RNA was isolated from L. esculentum leaf, fruit peel, and fruit flesh (pericarp and placenta) tissue and hybridized with probes for chalcone synthase A (CHS-A), chalcone synthase B (CHS-B), chalcone isomerase (CHI), flavanone 3-hydroxylase (F3H), and flavonol synthase (FLS). All five genes were expressed in leaf tissue (FIG. 1), while none of the genes were expressed in fruit flesh (data not shown). In the fruit peel, all genes were expressed except for CHI. The absence of CHI expression in the fruit peel and the lack of expression of all genes in the fruit flesh explains the lack of flavonol accumulation in the fruit. The data showing insignificant flavonol accumulation in tomato fruit has led investigators in the art to conclude that all tomatoes were blocked at the CHI step, and that traditional breeding programs would not succeed in producing enhanced levels of flavonol in the tomato fruit.

The present invention, however, recognizes that the biosynthesis pathway is expressed in the fruit peel and flesh of some wild tomato species, and that screening tomato germplasm for expression of one or more of the flavonol biosynthetic genes in the flesh, and/or CHI expression in the fruit peel provides a unique means for identifying appropriate breeding candidates.

Example III

Northern Blot Analysis of L. esculentum Breeding Lines

Figure 2:
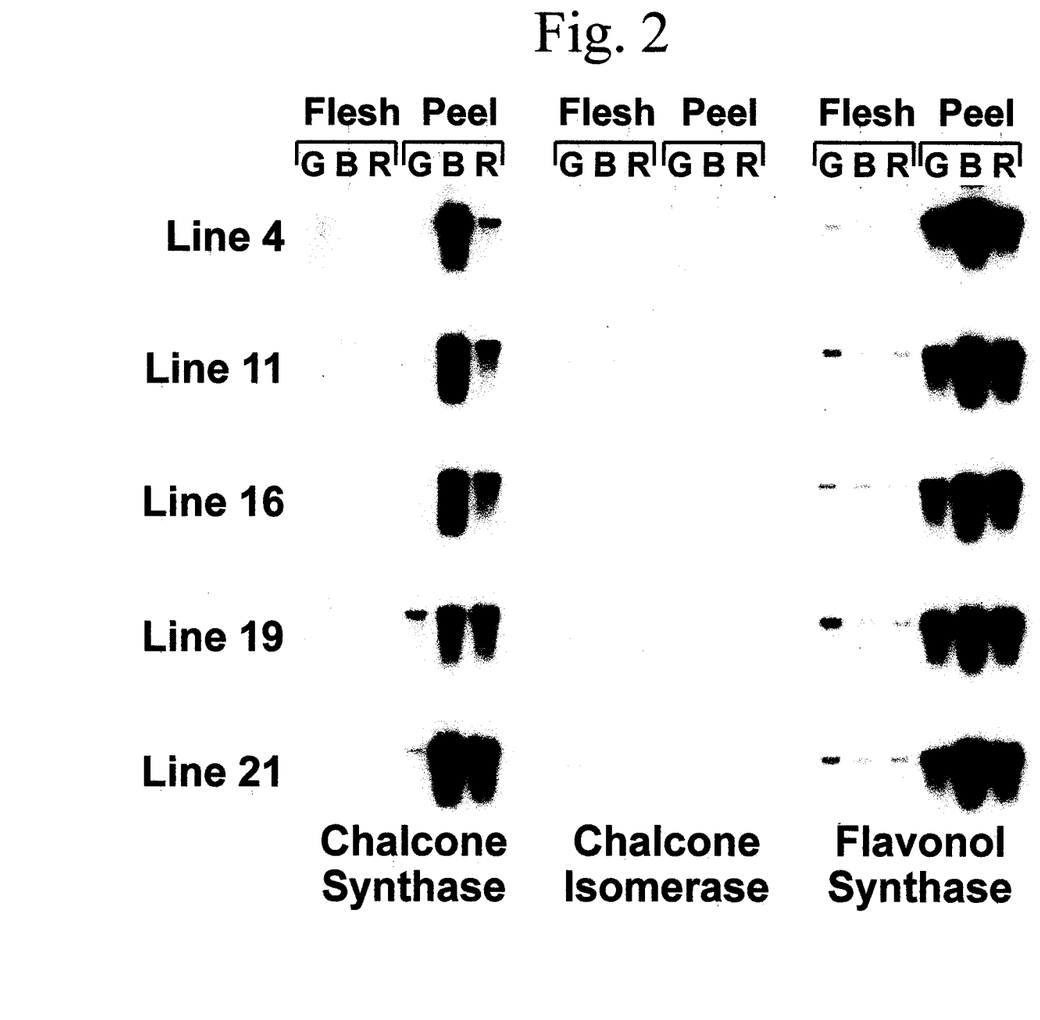
FIG. 2 shows flavonol biosynthetic gene expression in the peel and flesh of green (G), breaker (B), and red fruit (R) from three flavonol biosynthetic genes in *L. esculentum* breeding lines.

Northern analysis was carried out on five different L. esculentum breeding lines. Total RNA was isolated from peel or flesh tissue of green, breaker, or red tomatoes and hybridized with probes for CHS-A, CHI, or FLS. As mentioned previously, little or no expression of any of the genes was detected in the fruit flesh tissue (FIG. 2). For CHS-A and FLS, expression reached a peak in peel tissue of breaker tomatoes. No fruit-localized expression was detected for CHI in any of the analyzed lines. Flavonol analysis was carried out for an additional 17 lines, but no significant differences were detected (data not shown).

Example IV

Northern Analysis and Selection of Wild Lycopersicon Accessions

Northern analysis was also carried out on 13 wild Lycopersicon accessions, representing seven different species. The cultivated L. esculentum ZTV840 and the wild Lycopersicon accessions listed in Table 2 were grown and investigated for flavonol biosynthesis gene expression and flavonol accumulation.

Figure 3:
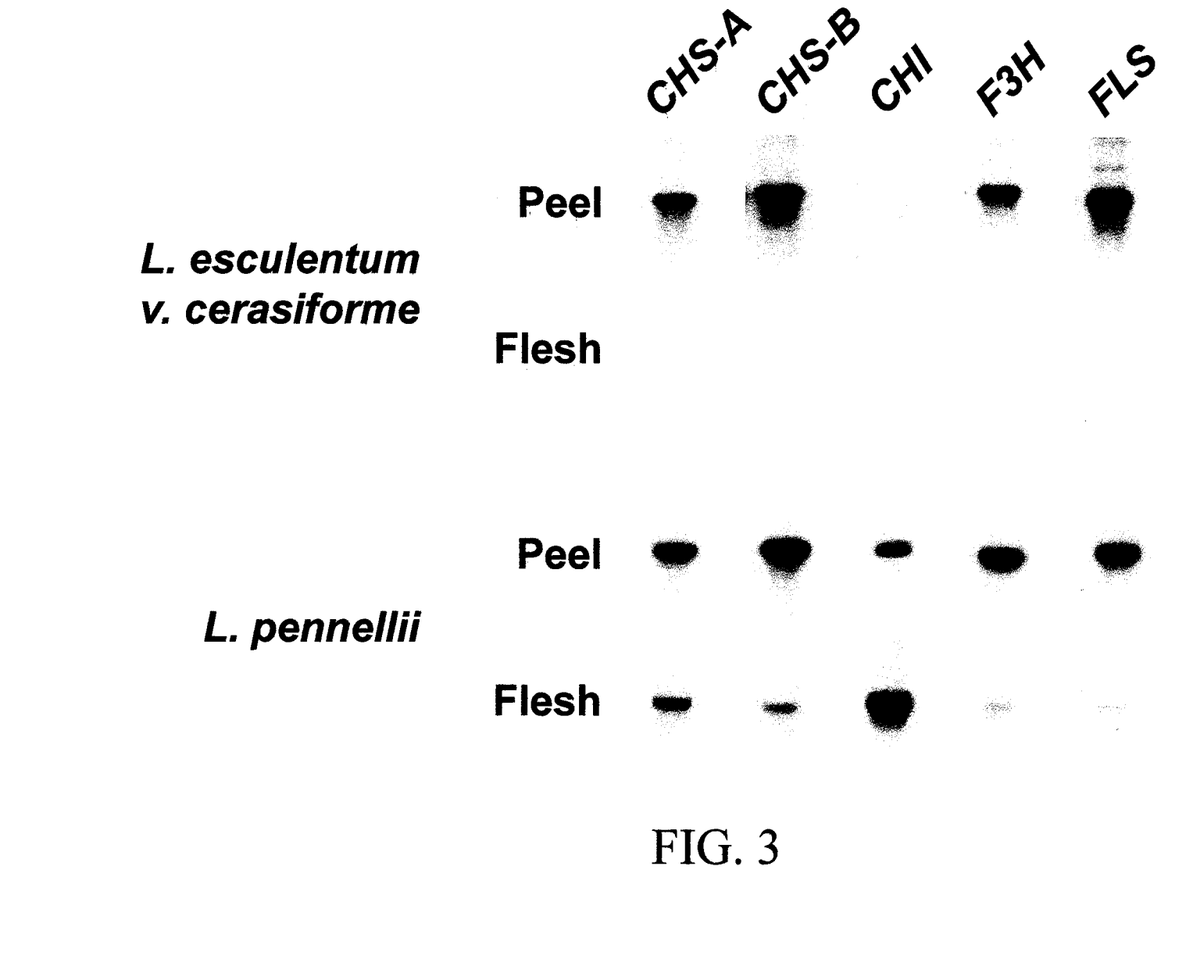
FIG. 3 shows flavonol biosynthetic gene expression in the peel and flesh of breaker fruit from five biosynthetic genes in *L. esculentum* v. *cerasiforme* (LA1286) and *L. pennellii* v. *puberulum* (LA1926).

As shown in Table 2 below and based on the Northern results, the wild accessions fell into two major classes: accessions with expression patterns similar to L. esculentum (LA1286, LA1673, LA722, LA1261, and LA2184) and accessions that exhibited CHI expression in the fruit peel (LA1963, LA2884, LA1926, LA111, LA1292, LA1330, LA1326, LA2727). Interestingly, three accessions (LA1963, LA2884, and LA1926) demonstrated expression of some or all of the flavonol biosynthetic genes in the tomato flesh tissue as well. FIG. 3 compares the Northern results from L. pennellii v. puberulum (LA1926) with those from L. esculentum v. cerasiforme (LA1286). This result clearly demonstrates that L. pennellii v. puberulum (LA1926) shows strong expression of all investigated flavonol biosynthetic genes in both the fruit peel and flesh. Therefore L. pennellii v. puberulum (LA1926) was chosen as a crossing partner to introgress flavonol production into L. esculentum.

TABLE 2

| Lycopersicon accessions | | CHI | | CHS, F3H, FLS | |
|---|---|---|---|---|---|
| | | Peel | Flesh | Peel | Flesh |
| L. esculentum (domesticated) | | | | X | |
| L. esculentum v. cerasiforme | LA1286 | | | X | |
| L. esculentum v. cerasiforme | LA1673 | | | X | |
| L. pimpinellifolium | LA722 | | | X | |
| L. pimpinellifolium | LA1261 | | | X | |
| L. pimpinellifolium | LA2184 | | | X | |
| L. chilense | LA1963 | X | X | X | X |
| L. chilense | LA2884 | X | X | X | X |
| L. pennellii v. puberulum | LA1926 | X | X | X | X |
| L. peruvianum | LA0111 | X | | X | |
| L. peruvianum f. glandulosum | LA1292 | X | | X | |
| L. chmielewskii | LA1330 | X | | X | |
| L. parviflorum | LA1326 | X | | X | |
| L. parviflorum | LA2727 | X | | X | |

It is understood that the terms "germplasm" and "accessions" are somewhat interchangeable, and use of the term "accession" is not meant to exclude from the method of the invention use of wild Lycopersicon plants that are not uniquely identified or part of a germplasm collection.

Example V

Analysis of Flavonol Accumulation in Wild Tomato Fruit

Flavonol analysis was carried out on the wild accessions in parallel with the Northern analysis (data not shown). However, only low concentrations of flavonols could be detected in the fruit, and if relied on by itself may lead an investigator to skip over the wild accessions that express the flavonol biosynthetic genes in the fruit flesh and peel as valuable breeding partners.

Example VI

Hybridization of L. esculentum and L. pennellii v. puberulum—Production of Domesticated Tomato Plants Pollen was collected from L. pennellii v. puberulum (LA1926), by inserting the tips of flowers into a small plastic tube, vibrating the flowers with an electric toothbrush, and shaking the pollen into the tube. Pollen collection was found to be the most successful early in the day when the relative humidity is at its low. The pollen was then transferred to the pistils of emasculated flowers of L. esculentum (ZTV840). The flowers of the L. esculentum were emasculated in order to prevent self-pollination. Floral buds were emasculated if they were large enough to be manipulated and the corolla tips had not separated. The fusion of the corolla and androecium of the flower forms a cap that covers the pistil or pollen recipient site. This cap was removed with forceps by inserting one tip between the style and anther and the other tip between the anther and calyx. Then by pulling slowly away from the floral axis, the cap was removed leaving only the thin style and pistil. The styles were then dipped into the plastic tube containing the pollen collected from the *L. pennellii* flowers, coating the pistils with the pollen. The emasculated flowers were then tagged, and all other naturally set fruit were removed from the calyx to ensure maximum fruit set from the controlled matings.

Fruits from crosses of *L. esculentum* and *L. pennellii* v. *puberulum* were harvested, and the seeds were separated from the locular gel. The seeds were washed with water and then dried at room temperature for two days.

Seeds were germinated in MetroMix 360. Young leaf tissue was used to prepare DNA by a standard DNA miniprep protocol. PCR primers were designed to anneal to the start and stop codons of the CHI coding region: forward primer, 5'-AAG GAT CCA TGG CGG TTG TTA CAA AAT TGC-3' (SEQ ID NO. 1) and reverse primer, 5'-AAA AGC TTA CTG GAC TGA CGA TAG CTC ACT TC-3' (SEQ ID NO. 2). PCR amplification of CHI from *L. esculentum* and *L. pennellii* v. *puberulum* results in different size products due to variations in intron structure between the two species. Therefore amplification with these primers provides a marker that distinguishes homozygous parents from heterozygous F1 plants. Ten putative F1 hybrids were screened using this PCR assay and were determined to be heterozygous at the CHI locus, which confirms the hybrid nature of these ten plants.

The F1 hybrids of the invention can be used to produce domesticated tomato plants that accumulate flavonols in the fruit flesh and peel. Traditional tomato breeding techniques are used. The particular breeding method is not critical to the invention, so long as the genetic factors responsible for CHI expression in the fruit peel and for upregulation of the biosynthesis pathway in the fruit flesh are stably incorporated into the genome of the tomato variety. Descriptions of traditional breeding techniques that are commonly used for different traits and crops can be found in one of several reference books (e.g., Allard, R. W., (1960) Principles of Plant Breeding; Simmonds, N. W., (1979) Principles of Crop Improvement; Sneep, J. et al., (1979) Plant Breeding Perspectives; Fehr, (1987) Principles of Cultivar Development—Theory and Technique).

Example VII

HPLC Determination of Flavonol Accumulation

Flavonol glycosides were extracted from lyophilized tomato fruit peel and flesh tissue of F1 hybrids. Approximately 100 mg of dry tissue was extracted overnight at a ratio of 80 μl of 80% methanol pH 2.0 (HCl) per 1 mgdwt tissue. Aliquots of this methanol extract were used for HPLC analysis of flavonol glycosides. For enzyme hydrolysis of glycosides, 1 ml of methanol extract was evaporated in vacuo at room temperature. Dried extracts were resuspended in 1 ml of 16% aqueous DMSO. Naringenase from Penicillium decumbens (Sigma-Aldrich) was added and incubated overnight at 35° C. Hydrolysis reactions were extracted with 50 μl HCl and 700 μA of ethyl acetate. Samples were vortexed for 30 seconds followed by 10 minutes of sonication. Separation of organic and aqueous phases was accomplished with a 2 minute, 15,000 rfc centrifugation step. The organic phase containing the aglycones was evaporated in vacuo at room temperature. Dried samples were resuspended in 100% methanol and used for HPLC analysis of flavonol aglycones.

Flavonol samples were analyzed on an HPLC system consisting of a 2690 Alliance separations module (Waters, Milford, Mass.) and a 996 PDA detector. For all analysis a 4.6 mm×150 mm Xterra $RP_{18}$ (5 μm) column protected by a $C_{18}$ Nova-pack guard column kept at 50° C. was used. Flavonoid standards were purchased from Indofine (Somerville, N.J.). The standards were dissolved in either methanol or DMSO and kept refrigerated at 4° C. HPLC grade acetonitrile from Fisher Scientific (Fair Lawn, N.J.) and water from a Milli-Q Water System from Millipore (Bedford, Mass.) were used as mobile phase. In all separations 1 ml of trifluoroacetic acid from Pierce (Rockford, Ill.) was added to 1 liter of the water used as mobile phase. For flavonol glycoside analysis, the gradient was 10-55% acetonitrile in 12 minutes at a flow-rate of 1.5 ml/min. For aglycone analysis, the gradient was 20-40% acetonitrile in 20 minutes at a flow-rate of 1.5 ml/min. Quantification was performed using peak area of external standard mixtures with known concentrations ranging from 100 ng to 4000 ng of standard compound per injection.

Figure 4:
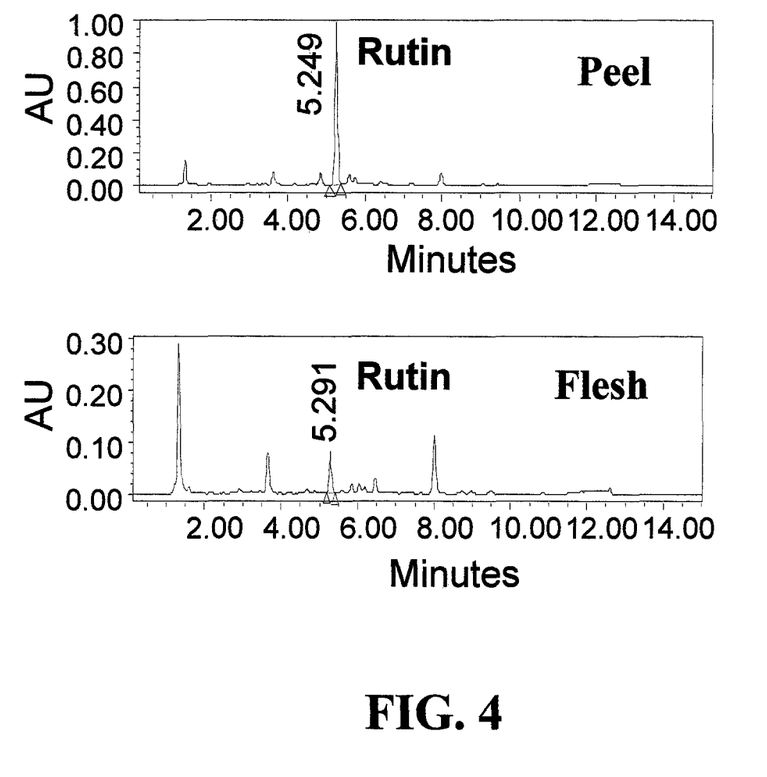
FIG. 4 shows an HPLC analysis of flavonol content in the flesh and peel of the fruit of a plant resulting from a hybrid cross between *L. esculentum* and *L. pennellii* v. *puberulum*.
Figure 5:
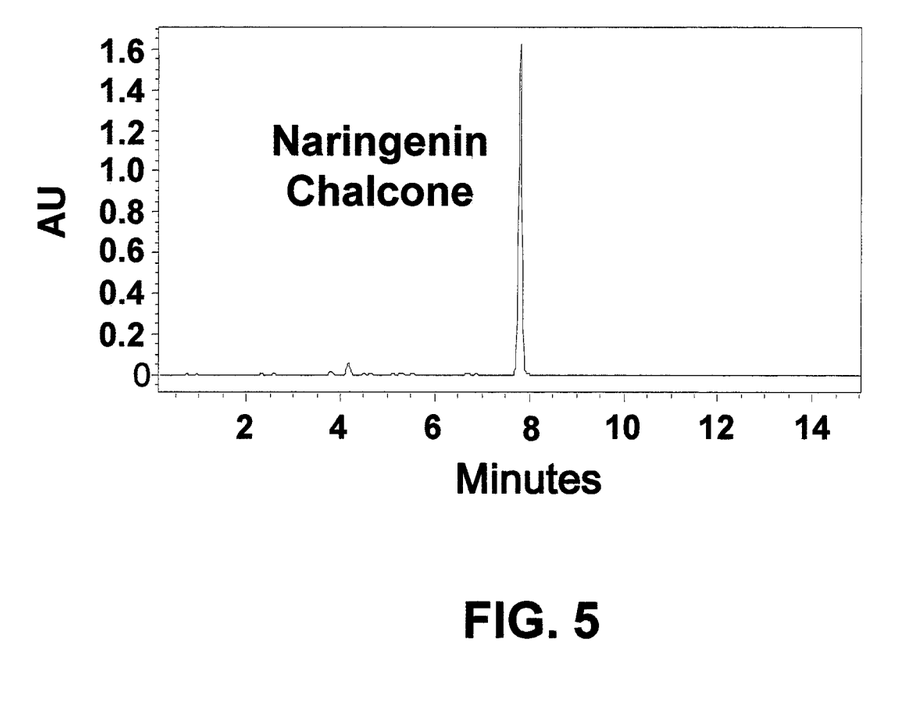
FIG. 5 shows accumulation of naringenin chalcone in the fruit peel in *L. esculentum* by HPLC analysis.

FIG. 4 shows a HPLC analysis of the flavonol content in the flesh and peel of the fruit of a plant resulting from a hybrid cross between *L. esculentum* and *L. pennelli* v. *puberulum*. A control HPLC analysis of *L. esculentum* fruits shows the expected accumulation of naringenin chalcone, with no accumulation of flavonols (FIG. 5). Clearly, the introduction of the genetic factors from *L. pennellii* into the hybrid plant results in the expression of the flavonol biosynthetic genes and subsequent production of flavonols and flavonol glucosides in the peel and also in the flesh. Analysis of the HPLC data is shown in Table 3 below, where the accumulation of flavonols in both the peel and flesh is significantly enhanced compared to a standard domesticated tomato, *L. esculentum*.

TABLE 3

| | Flavonol Content μg/mgdwt | | Estimated Total Flavonol Content |
|---|---|---|---|
| | Peel | Flesh | (mg) in a 57 g tomato |
| *L. esculentum* | 3 | 0.1 | 1.2 |
| *L. esculentum* X *L. pennellii* v. *puberulum* | 17 | 2 | 12 |

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A method of making a hybrid *Lycopersicon* plant expressing enhanced flavonol in the peel and flesh of the fruit of said plant, the method comprising:
    (a) screening a *Lycopersicon* accession for expression of chalcone isomerase (CHI) in the peel and for expression of one or more of the genes of the flavonol biosynthetic pathway in the flesh, wherein said *Lycopersicon* accession is a *L. chilense* or *L. pennellii* accession;
    (b) crossing the *L. chilense* or *L. pennellii* accession identified in (a) that expresses CHI in the peel and that expresses genes of the flavonol biosynthetic pathway in the flesh with a *L. esculentum* plant to produce progeny hybrid *Lycopersicon* plants, wherein said genes of the flavonol biosynthetic pathway comprise chalcone synthase (CHS), CHI, flavanone 3-hydroxylase (F3H) and flavonol synthase (FLS); and
    (c) selecting said progeny hybrid *Lycopersicon* plants for a hybrid *Lycopersicon* plant that expresses enhanced flavonol in the peel and the flesh when compared to the *L. esculentum* plant of (b), to thereby make a hybrid *Lycopersicon* plant expressing enhanced flavonol in the peel and flesh of the fruit of said plant.

2. The method of claim 1, wherein the method further comprises harvesting fruit from the hybrid *Lycopersicon* plant.

3. The method of claim 2, wherein the method further comprises collecting seed from the harvested fruit.

4. The method of claim 1, wherein the hybrid *Lycopersicon* plant accumulates flavonol in the fruit flesh of the plant at a level greater than 0.5 µg/mgdwt.

5. The method of claim 1, wherein the hybrid *Lycopersicon* plant accumulates flavonol in the fruit flesh of the plant at a level greater than 1.0 µg/mgdwt.

6. The method of claim 1, wherein the hybrid *Lycopersicon* plant accumulates flavonol in the fruit flesh of the plant at a level greater than 1.5 µg/mgdwt.

7. The method of claim 1, wherein the flavonol content in the fruit peel of the hybrid *Lycopersicon* plant is at least 5 µg/mgdwt.

8. The method of claim 1, wherein the flavonol content in the fruit peel of the hybrid *Lycopersicon* plant is at least 10 µg/mgdwt.

* * * * *

SEQUENCE LISTING

<160> NUMBER OF SEQ ID NOS: 2

<210> SEQ ID NO 1
<211> LENGTH: 30
<212> TYPE: DNA

```
<213> ORGANISM: Artificial Sequence
<220> FEATURE:
<223> OTHER INFORMATION: DNA primer synthesized

<400> SEQUENCE: 1
aaggatccat ggcggttgtt acaaaattgc                              30

<210> SEQ ID NO 2
<211> LENGTH: 32
<212> TYPE: DNA
<213> ORGANISM: Artificial Sequence
<220> FEATURE:
<223> OTHER INFORMATION: DNA primer synthesized

<400> SEQUENCE: 2
aaaagcttac tggactgacg atagctcact tc                           32
```